United States Patent
Calderon

(10) Patent No.: US 7,323,118 B2
(45) Date of Patent: Jan. 29, 2008

(54) COMPOSITION OF HYPOCHLOROUS ACID AND ITS APPLICATIONS

(75) Inventor: Justo Leonardo Calderon, Bogotá (CO)

(73) Assignee: Aquilabs S.A., Bogota (CO)

( * ) Notice: Subject to any disclaimer, the term of this patent is extended or adjusted under 35 U.S.C. 154(b) by 357 days.

(21) Appl. No.: 10/467,121

(22) PCT Filed: Oct. 1, 2001

(86) PCT No.: PCT/IB01/02085

§ 371 (c)(1),
(2), (4) Date: Aug. 5, 2003

(87) PCT Pub. No.: WO03/028741

PCT Pub. Date: Apr. 10, 2003

(65) Prior Publication Data

US 2004/0062818 A1    Apr. 1, 2004

(51) Int. Cl.
*C01B 11/06* (2006.01)
(52) U.S. Cl. .................................. 252/187.32
(58) Field of Classification Search ..................... None
See application file for complete search history.

(56) References Cited

U.S. PATENT DOCUMENTS 6,426,066 B1    7/2002    Najafi et al.

OTHER PUBLICATIONS

Joe B. Selkon; Improvements In or Relating to Sterilising Preperations; Mar. 1, 2001; International Application Published Under the PCT; WO 01/13926.*

William A. Rutala and David J. Weber; Uses of Inorganic Hypochlorite (Bleach) in Health-Care Facilities; Oct. 1997; Clinical Microbiology Reviews; pp. 597-610.*

R.-Y. Zhuang, L.R. Beuchat, and F.J. Angulo; Fate of Salmonella montevideo on and in Raw Tomatoes as Affected by Temperature and Treatment with Chlorine; Jun. 1995; Applied and Enviromental Microbiology; pp. 2127-2131.*

Joe B. Selkon; Improvements In or Relating to Sterilising PreperaUons; Mar. 1, 2001; International Application Published Under the PCT; WO 01/13926 (See previously supplied copy-IDS).*

* cited by examiner

*Primary Examiner*—Johann Richter
*Assistant Examiner*—Ali Soroush
(74) *Attorney, Agent, or Firm*—Welsh & Katz, Ltd.

(57) ABSTRACT

Composition of Hypochlorous acid characterized because it has the following chemical composition Hypochlorous acid 6.5-7.3%
Hydrochloric acid 27.6-28.5%
Sodium chloride 13.6-14.2%
Sodium hypochlorite 34.8-35.4%
Chlorine in solution 7-6.5%
Dissolved oxygen 10.5-8.1%

The composition of hypochlorous acid has medical application in humans and in veterinary practice, both prophylactic and therapeutic. It can also be applied in antisepsis and sterilization of foods and in the treatment of water and water supply systems. In flower growing is can be used for the disinfection of crops and the elimination of fusarium and sigatoka negra.

9 Claims, No Drawings

US 7,323,118 B2

COMPOSITION OF HYPOCHLOROUS ACID AND ITS APPLICATIONS

TECHNICAL

This Application for a Patent of Invention refers to a Composition of Hypochlorous Acid and its different applications especially in the field of medicine, such as prophylactic and therapeutic treatment for control of infections.

BACKGROUND

After 1915, and as a result of the Great War, more than 200 bacterial action compounds were studied, among them hypochlorous acid. It was initially detected as an oxidating agent generated by neutrophiles. It was obtained from seawater.

There are references of studies by Dakin in 1917 with sodium hypochlorite diluted to 0.50% as an irrigation liquid for the cleaning and disinfection of contaminated wounds.

Later, in 1958, Agnes investigated hypochlorous acid as an immunological substance and defense mechanisms for granulocytes.

In 1989 Stephan J,. Weiss in the New England Journal of medicine conducted bacterial sensitivity studies on $E.\ Coli$ and toxicity on tissue in guinea-pigs.

There are currently several patents of invention related to the production of hypochlorous acid, as mentioned below:

U.S. Pat. No. 4,190,638 "Production of hypochlorous acid", owned by PPG Industries Inc., of Feb. 26, 1980 in which aqueous acid is produced by precipitating the acid through carbonation in a electrolytic cell where the cathode is liquid which is placed in contact with a bed fluidized with a mixture of gaseous chlorine and water vapor where the gas which is formed from the hypochlorous bed is absorbed by the water.

U.S. Pat. No. 4,908,215 "Hypochlorite compositions containing thiosulphate and their use" of Mar. 13, 1990, which discloses a process for disinfection, sterilization, bleaching and cleaning of a liquid or a surface comprised of: (a) producing an aqueous solution of hypochlorite, thiosulphate of earthy alkaline metal and a prebuffer in which the hypochlorite has an initial concentration of about 5 to 5000 ppm of chlorine and a molar ratio of thiosulphate to hypochlorite between 0.25:1 and 0.75: 1; (b) adjusting the initial pH of the solution between 9,.0 and 11.0 in contact with the surface or the liquid with the solution until the hypochlorite is consumed and the pH of the prebuffer solution decreases while the hypochlorite is consumed by the thiosulphate at the same time as the hypochlorite begins to depend on the initial pH of the solution.

U.S. Pat. No. 5,027,627 "Production of Hypochlorous Acid" published on Aug. 6, 1991, where hypochlorous acid is obtained by reaction of an aqueous solution of an alkaline metal hydroxide, forming drops with the gaseous chlorine to produce hypochlorous acid in vapor and particles of solid alkaline metal; a process where the molar ratio of the gaseous chlorine to the alkaline metal hydroxide is kept at least 22:1, The process includes the formation of impure chlorate in chlorinated alkaline metal particles. The hypochlorous acid produced contains 35-60% of weight dissolved in concentrated chlorine of at least about 2% by weight and is substantially free of ions of the alkaline metal and chlorine.

U.S. Pat. No. 5,322,677 "Process for the production of a concentrated solution of hypochlorous acid", owned by Oil Corporation, published on Jun. 21, 1994, a process which consists of the obtaining of an aqueous hypochloric acid solution having an HOCl concentration of 50-60% by weight, which comprises making a aqueous solution of an alkaline metal hydroxide with 50% by weight with excess of chlorine gas react, making them react at 80-120 deg. C. to produce a mixture of monoxide, chlorine, hypochlorous acid vapor and water vapor, solid particles of chlorate alkaline metal of at least 10%.

WO 9514636 "Manufacture of Hypochlorous Acid" owned by Joseph Repman, The Dow Chemical Company Trent and David, L., published Jun. 1, 1995, a process which consists of placed in contact the drops of a aqueous solution of hypochlorite metal having an intermediate volume, a diameter of 500 mm with chlorine gas to produce hypochlorous acid, vaporization of 20% m of hypochlorous acid produced in the preceding stage, containing chlorine, water vapor, hypochlorous acid and dichloride monoxide within an aqueous phase of acid.

ADVANTAGES OF THE INVENTION

The patent of invention Composition of Hypochlorous Acid and its various applications has the following advantage over others in the state of the art:

- The composition of hypochlorous acid is not toxic and does not attack the skin
- The composition is fully biodegradable
- Disinfection occurs in seconds given the broader disinfection spectrum
- As a deodorant it destroys organic particles since it attacks mercaptane, methane and hydrosulphuric gases.
- It has bacteriostatic powers for up to 24 hours
- The process if obtaining the composition is economical, due to its ample dilution.

DISCLOSURE OF THE INVENTION

The concern to find substances which do not cause reactions in the organism and are highly effective in combating microorganisms resistant to antimicrobial agents and drugs has led to the study of hypochlorous acid, a substance which as the characteristics of minimizing morbidity and mortality produced by bacterial infections in comparison with normal saline solutions, a substance mostly used for washing the abdominal cavity and tissues.

Hypochlorous acid (HOCl) is a bactericide oxidant known particularly as an aqueous solution which attacks microorganisms in the place where they are produced, dependent on 02. In particular, it reacts modifying various high-density proteins (aminoacids, lipids) which are first found in the plasma or the proteins of the plasmatic membrane, inhibiting synthesis.

Hypochlorous acid is an unstable compound, highly reactive, the strongest of the hypo halogenated acids and one of the most powerful oxidating agents among chlorate oxacids. It is a weak acid with a dissociation constant of 2.9+10−8 at 25 deg. C., it is stable in cold diluted and pure solutions. The acid reacts with peroxide and gives off oxygen.

Half of the protein is highly toxic to cells; it deactivates or inhibits several systems of the endoplasmatic reticule carrier (transport of glucose, several transporters of amino acids, Na+/K-ATPase.) and generally causes harm to small molecules, making the cell inflate and subsequently causing cell death.

It can cause the death of highly resistant bacterial spores, all types of virus, macrobacterium with serous capsule (TB), all other vegetative bacteria and fungi in a concentration of 0.2% compared to other high-level microbicide substances such as alkaline glutaraldehyde at 2% or hydrogen peroxide. HOCl can damage isolated DNA, cell death precedes oxidation of DNA in whole cells, and the sum of mieloperoxide inhibits induced oxygen peroxide H2O2 and breaks down the DNA structure.

Chlorine concentrations of 0.25 which are effective bactericides for many microorganisms except microbacteria, which are 500 times more resistant. Organic material in great part reduces antimicrobial activity of chlorine.

It is a bactericide agent which attacks microorganisms at the place where they proliferate, prepared in the immune system by nuclear polymorph neutrophiles which migrate and adhere to the endothelial cells to act as a mediator in inflammation, increasing the permeability of the vascular endothelium for cellular participation and to kill antigens. This substance is produced by hydrogen peroxide (H2O2), a chlorine ion, in reaction with the enzyme mieloperoxidase.

Mieloperoxidase converts H2O2 into a reasonable microbicidal agent and HOCl into an excellent one; at the same time it diverts the genotoxic H2O2 into HOCl which is highly toxic for the tissue in a free protein system, but which is considerably less toxic in vivo.

The composition of hypochlorous acid object of this patent of invention is a solution of hypochlorous acid with a content of 17 g/l of available chlorine. The physical properties are as follows:

| | |
|---|---|
| Formula | HOCl |
| Appearance | Crystalline |
| Odor | Characteristic of chlorine |
| Chlorine (g/l) | Max 16-18 |
| pH | 5-6 |
| Density (g/ml) | 0.9-1-05 |
| Solids | None |
| ORP | 1250-1450 mv |

The chemical composition is:
Hypochlorous acid 6.5-7.3%
Hydrochloric acid 27.6-28.5%
Sodium chloride 13.6-14.2%
Sodium hypochlorite 34.8-35.4%
Chlorine in solution 7-6.5%
Dissolved oxygen 10.5-8.1%
The stability of the solution depends on:
Chlorine concentration
pH of the solution
Temperature of the solution
Exposure to light
The spectrum shown by the composition of hypochlorous acid is as follows:
HIV
*Staphylococcus aureus*
Hemolitic Streptococcus
*Coagulaze staphylococcus* (−Y+)
*Enterobacter aerogenes*
Salmonella
Clostridium
*Aspergillus flavus*
Bacillus SPP
Pseudomonas
Pulmonary Klebsiella
*Escherichia Coli*

The tissular action of the composition of hypochlorous acid is particularly notable in three areas:

1. Antiseptic: direct germicidal action, like any other chlorate. This action is a known and classic one
2. Granulant: through a local increase in the repair cells, since studies have shown a local increase in fibroblasts.
3. Local increase in immunological activity; when the action of the granulosites is triggered locally. It is well-known that the two principal mechanisms of defense of the neutrophiles and other defensive cells are the production of oxidants which fire off at the aggressor germ: peroxides and hypochlorous acid.

APPLICATIONS OF THE COMPOSITION

The composition of hypochlorous acid, object of this application for a patent of invention, in the field of medicine, has its principal application in:

1.—Medical 1.2 Therapy 1.1.1 For antisepsis and granulation of infected tissues, abscesses, cellulitis etc. With excellent results for curing infectious events of subcutaneous cell tissue, whether with open or closed tissue or with no wound.

1.2.1 Ulcers on the lower limbs. The surface should remain in contact with the product 1.3.1 Exposed surfaces and open cuts, in infected cavities such as peritonitis and empyema 1.4.1 In infectious sinusitis and rhinitis 1.5.1 Intra-articular for treatment of septic arthritis. Use in orthopedic-osseous infectious events 1.2 Prophlaxis a) Washing of clean and contaminated surgical wounds b) Local cleaning of the peritoneal cavity for appendicitis and colecystitis, in rdumentary form c) Antisepsis of surfaces and elements 2. Non Medical
  1. Antisepsis and sterilization of food
  2. Treatment of water and water supply systems.
  3. Disinfection of crops.
  4. Elimination of fusarium and sigatoka negra.

EXAMPLES OF APPLICATION

Abdominal Surgery 300 trials of the composition of hypochlorous acid at 5000 ppm have been effected in the systematic washing of surgical wounds and of the peritoneal cavity, local or generalized.

Wounds were evaluated, along with evolution by Swan's table of classification of infection of surgical wounds.

The results were:

An average of 4 washes was required with only the hypochlorous acid composition, a laparotomy closing was achieved with an average of 5-15 washes Cultures were negativized with the third wash and 4 *E Coli* and 2 Pseudonomes were obtained. Neither re-laparotomy nor abscesses were necessary The index of infection of the surgical wound fell to 1.0% (10%-25% in different series) for appendicectomy in different studies.

The results are detailed in the chart below:

|  | Without peritonitis | Localized peritonitis | Generalized peritonitis | Laparostomy |
|---|---|---|---|---|
| Edematose appendicitis | 60 | | | |
| Suppurative appendicitis | 92 | 58 | | |
| Perforated appendicitis | | 38 | 22 | 4 |
| Perforated colon diverticulus | | | | 3 |
| Multiple wound laparotomy | | 10 | 10 | |
| Septic uterine perforation | | | 1 | |

Vascular Pathology of Lower Limits

Over 2090 cases were handled. The hypochlorous acid composition was used at 5% un ulcerous lesions of arterial/venous origin, surgical wounds, prophylactic and therapeutic amputations, it being recommended that the affected zone be kept damp with the liquid, for local use only.

Specific studies were performed on patients with more prolonged use for kidney, liver and modular functions, without finding any alteration in these organs.

In addition there were toxicology studies, and no levels of hypochlorous acid were found in urine or blood.

Biopsies were evaluated by pathology, showing the effected described previously by other authors, of a local increase in fibroblasts in comparison to patients not using the composition.

The results were:

As with the abdominal pathology, it is difficult to standardize on the basis of size, depth, origin and state of the ulcerations. Consideration was given to:

Excellent/very good: 88%, where there was full cure of the ulcers including refractory lesions from all prior treatment, infected wounds, traumatic necrosis and ischaemias.

Fair: 12%, given by the appearance of granulation tissue and reduction of the ulcerated area, but without full closure or cure.

There were reactions considered adverse by erythema of the skin of bronchial spasm in 1.5% but these ceased when use was suspended in the first case.

Cultures and tests of inhibition for staphylococcus aureus, *E. Coli* and pseudomona were conducted and there was full inhibition in the growth of all three bacteria when adding hypochlorous acid to the culture agar and in the Petri box, inhibition haloes.

The invention claimed is:

1. A composition of hypochlorous acid having the following chemical composition: hypochlorous acid 6.5-7.3%, hydrochloric acid 27.6-28.5%, sodium chloride 136-14.2%, sodium hypochlorite 34.8-35.4% chlorine in solution 6.5-7%, dissolved oxygen 8.1-10.5%.

2. The composition of hypochlorous acid of claim 1 having the following physical properties: pH 5-6, Density (g/ml) 0.9-1.05. Solids Nones, ORP 1250-1450 mV.

3. The composition of hypochlorous acid of claim 1 where the amount of chlorine varies from 16 g/l to 18 g/l.

4. The composition of hypochlorous acid of claim 1 where said composition has therapeutic medical application in human beings: a) for antisepsis and granulation of infected tissues, abscesses, and cellulitis; b) ulcers on the lower limbs; c) exposed surfaces and open cuts infected cavities such as peritonitis and empyema; d) in infectious sinusitis and rhinitis; and e) intra-articular for treatment of septic arthritis.

5. The composition of hypochlorous acid of claim 1 where said composition has medical application in humans: a) washing of clean and contaminated surgical wounds; b) local cleaning of the peritoneal cavity for appenficitis and cholecystitis, in rudimentary form; and c) antisepsis of surfaces and elements.

6. The composition of hypochlorous acid of claim 1, where said composition has applications in: a) antisepsis and sterilization of food; and b) treatment of water and water supply systems.

7. The composition of hypochlorous acid of claim 1 where said composition has uses in veterinary practice for: a) washing of clean and contaminated surgical wounds; and b) antisepsis of surfaces and elements.

8. The composition of hypochlorous acid in claim 1 where said composition has veterinary application in therapy: a) for antisepsis and granulation of infected tissues, abscesses; and b) ulcerations of all types.

9. The composition of hypochlorous acid in claim 1 where said composition has applications in flower-growing: a) to disinfect crops; and b) to eliminate fusarium and sigatoka negra.

* * * * *